US008821541B2

(12) United States Patent
Dreyfuss et al.

(10) Patent No.: US 8,821,541 B2
(45) Date of Patent: Sep. 2, 2014

(54) SUTURE ANCHOR WITH INSERT-MOLDED RIGID MEMBER

(75) Inventors: Peter J. Dreyfuss, Naples, FL (US); William C. Benavitz, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1023 days.

(21) Appl. No.: 11/518,872

(22) Filed: Sep. 12, 2006

(65) Prior Publication Data
US 2007/0073299 A1   Mar. 29, 2007

Related U.S. Application Data

(63) Continuation-in-part of application No. 11/097,172, filed on Apr. 4, 2005, now Pat. No. 8,343,186, and a continuation-in-part of application No. 10/083,568, filed on Feb. 27, 2002, now Pat. No. 7,226,469, which is a continuation-in-part of application No. 09/495,816, filed on Feb. 2, 2000, now Pat. No. 6,517,564, application No. 11/518,872, which is a continuation-in-part of application No. 11/224,060, filed on Sep. 13, 2005.

(60) Provisional application No. 60/271,414, filed on Feb. 27, 2001, provisional application No. 60/118,228, filed on Feb. 2, 1999, provisional application No. 60/125,781, filed on Mar. 23, 1999, provisional application No. 60/715,614, filed on Sep. 12, 2005.

(51) Int. Cl.
*A61B 17/04* (2006.01)
*A61B 17/86* (2006.01)

(52) U.S. Cl.
CPC ......... *A61B 17/0401* (2013.01); *A61B 17/8645* (2013.01); *A61B 2017/0427* (2013.01); *A61B 2017/0414* (2013.01); *A61B 2017/044* (2013.01); *A61B 2017/0412* (2013.01)
USPC ........................................ 606/232

(58) Field of Classification Search
USPC .............. 606/232, 72–74; 411/320, 142, 199, 411/216, 356, 357, 76, 350, 555
See application file for complete search history.

(56) References Cited

U.S. PATENT DOCUMENTS 1,610,309 A   12/1926   Niederer
1,925,174 A    9/1933   Cremean (Continued)

FOREIGN PATENT DOCUMENTS

CA    2045903       6/1991
EP    0951869 A1   10/1999

(Continued)

OTHER PUBLICATIONS

European Search Report for EP Application No. 05102676.3 dated Aug. 29, 2005.

(Continued)

*Primary Examiner* — Dianne Dornbusch
(74) *Attorney, Agent, or Firm* — Carlson, Gaskey & Olds, P.C.

(57) ABSTRACT

A threaded suture anchor with an eyelet shield transversely molded at a distal end of the anchor body, over which one or more strands of suture is looped. The anchor body is threaded and has a tapered distal portion. The proximal end portion of the suture anchor body has a polygonally shaped opening to accept a polygonal drive head, preferably hexagonal or square. The peripheral surface defining polygonally shaped opening is rounded and smooth to prevent abrading sutures placed in contact therewith. In another embodiment, a push-in anchor is provided with an eyelet shield at the proximal end of the anchor.

11 Claims, 8 Drawing Sheets

(56) References Cited

U.S. PATENT DOCUMENTS

| | | | |
|---|---|---|---|
| 2,045,903 A | 6/1936 | Fortin | |
| 2,121,193 A | 6/1938 | Hanicke | |
| 2,329,398 A | 9/1943 | Duffy | |
| 2,381,050 A | 8/1945 | Hardinge | |
| 2,490,364 A | 2/1948 | Livingston | |
| 2,472,103 A | 6/1949 | Giesen | |
| 2,562,419 A | 7/1951 | Ferris | |
| 2,699,774 A | 1/1955 | Livingston | |
| 3,143,916 A | 8/1964 | Rice | |
| 3,420,929 A * | 1/1969 | Morin | 264/278 |
| 3,716,058 A * | 2/1973 | Tanner, Jr. | 606/221 |
| 3,768,635 A | 10/1973 | Eggert | |
| 3,842,825 A | 10/1974 | Wagner | |
| 3,861,269 A | 1/1975 | Laverty | |
| 3,910,281 A | 10/1975 | Kletschka et al. | |
| 3,951,261 A | 4/1976 | Mandel et al. | |
| 3,990,438 A | 11/1976 | Pritchard | |
| 4,006,747 A | 2/1977 | Kronenthal et al. | |
| 4,013,071 A | 3/1977 | Rosenberg | |
| 4,135,623 A | 1/1979 | Thyen | |
| 4,175,555 A | 11/1979 | Herbert | |
| 4,244,370 A | 1/1981 | Furlow et al. | |
| 4,275,717 A | 6/1981 | Bolesky | |
| 4,289,124 A | 9/1981 | Zickel | |
| 4,301,551 A | 11/1981 | Dore et al. | |
| 4,351,069 A | 9/1982 | Ballintyn et al. | |
| 4,424,898 A | 1/1984 | Thyen et al. | |
| 4,454,875 A | 6/1984 | Pratt et al. | |
| 4,467,478 A | 8/1984 | Jurgutis | |
| 4,483,023 A | 11/1984 | Hoffman, Jr. et al. | |
| 4,507,817 A | 4/1985 | Staffeld | |
| 4,519,100 A | 5/1985 | Wills et al. | |
| 4,520,511 A | 6/1985 | Gianezio et al. | |
| 4,537,185 A | 8/1985 | Stednitz | |
| 4,539,981 A | 9/1985 | Tunc | |
| 4,590,928 A | 5/1986 | Hunt et al. | |
| 4,597,776 A | 7/1986 | Ullman et al. | |
| 4,605,414 A | 8/1986 | Czajka | |
| 4,631,100 A | 12/1986 | Pellegrino | |
| 4,632,100 A | 12/1986 | Somers et al. | |
| 4,633,869 A | 1/1987 | Schmieding | |
| 4,640,271 A | 2/1987 | Lower | |
| 4,672,957 A | 6/1987 | Hourahane | |
| 4,693,654 A | 9/1987 | Bettini | |
| 4,712,542 A | 12/1987 | Daniel et al. | |
| 4,723,541 A | 2/1988 | Reese | |
| 4,738,255 A | 4/1988 | Goble et al. | |
| 4,741,330 A | 5/1988 | Hayhurst | |
| 4,750,492 A | 6/1988 | Jacobs | |
| 4,756,653 A | 7/1988 | Berger | |
| 4,784,126 A | 11/1988 | Hourahane | |
| 4,815,467 A | 3/1989 | Chestnut | |
| 4,870,957 A | 10/1989 | Goble et al. | |
| 4,898,156 A | 2/1990 | Gatturna et al. | |
| 4,946,467 A * | 8/1990 | Ohi et al. | 606/228 |
| 4,946,468 A | 8/1990 | Li | |
| 4,963,144 A | 10/1990 | Huene | |
| 4,976,715 A | 12/1990 | Bays et al. | |
| 4,988,351 A | 1/1991 | Paulos et al. | |
| 5,002,550 A * | 3/1991 | Li | 606/139 |
| 5,002,563 A * | 3/1991 | Pyka et al. | 606/222 |
| 5,019,079 A | 5/1991 | Ross | |
| 5,037,422 A | 8/1991 | Hayhurst et al. | |
| 5,041,129 A | 8/1991 | Hayhurst et al. | |
| 5,047,030 A | 9/1991 | Draenert | |
| 5,059,201 A | 10/1991 | Asnis | |
| 5,061,181 A | 10/1991 | Niznick | |
| 5,067,956 A | 11/1991 | Buford, III et al. | |
| 5,100,417 A | 3/1992 | Cerier et al. | |
| 5,100,471 A | 3/1992 | Winnik et al. | |
| 5,102,414 A | 4/1992 | Kirsch | |
| 5,102,421 A | 4/1992 | Anspach, Jr. | |
| 5,139,499 A | 8/1992 | Small et al. | |
| 5,141,520 A | 8/1992 | Goble et al. | |
| 5,152,790 A | 10/1992 | Rosenberg et al. | |
| 5,156,616 A | 10/1992 | Meadows et al. | |
| 5,163,960 A | 11/1992 | Bonutti | |
| 5,176,682 A | 1/1993 | Chow | |
| 5,180,382 A | 1/1993 | Frigg et al. | |
| 5,207,679 A | 5/1993 | Li | |
| 5,217,486 A | 6/1993 | Rice et al. | |
| 5,224,946 A | 7/1993 | Hayhurst et al. | |
| 5,236,445 A | 8/1993 | Hayhurst et al. | |
| 5,242,447 A | 9/1993 | Borzone | |
| 5,246,441 A | 9/1993 | Ross et al. | |
| 5,250,055 A | 10/1993 | Moore et al. | |
| 5,258,016 A | 11/1993 | DiPoto et al. | |
| 5,261,914 A * | 11/1993 | Warren | 606/323 |
| 5,268,001 A | 12/1993 | Nicholson et al. | |
| 5,275,176 A | 1/1994 | Chandler | |
| 5,285,016 A | 2/1994 | Narizuka et al. | |
| 5,306,290 A | 4/1994 | Martins et al. | |
| 5,312,438 A | 5/1994 | Johnson | |
| 5,320,626 A | 6/1994 | Schmieding | |
| 5,327,896 A | 7/1994 | Schmieding | |
| 5,330,468 A | 7/1994 | Burkhart | |
| 5,336,240 A | 8/1994 | Metzler et al. | |
| 5,350,383 A | 9/1994 | Schmieding et al. | |
| 5,364,400 A | 11/1994 | Rego et al. | |
| 5,370,662 A | 12/1994 | Stone et al. | |
| 5,375,956 A | 12/1994 | Pennig | |
| 5,380,334 A | 1/1995 | Torrie et al. | |
| 5,383,905 A | 1/1995 | Golds et al. | |
| D357,534 S | 4/1995 | Hayes | |
| 5,403,136 A | 4/1995 | Mathys | |
| 5,411,506 A | 5/1995 | Goble et al. | |
| 5,417,533 A | 5/1995 | Lasner | |
| 5,417,691 A | 5/1995 | Hayhurst | |
| 5,417,712 A * | 5/1995 | Whittaker et al. | 606/232 |
| D359,557 S | 6/1995 | Hayes | |
| 5,423,860 A | 6/1995 | Lizardi et al. | |
| 5,441,502 A | 8/1995 | Bartlett | |
| 5,441,508 A | 8/1995 | Gazielly et al. | |
| 5,443,482 A | 8/1995 | Stone et al. | |
| 5,447,401 A | 9/1995 | Jones et al. | |
| 5,456,685 A | 10/1995 | Huebner | |
| 5,462,644 A | 10/1995 | Woodson | |
| 5,464,427 A | 11/1995 | Curtis et al. | |
| 5,466,243 A | 11/1995 | Schmieding et al. | |
| 5,470,334 A | 11/1995 | Ross et al. | |
| 5,480,403 A | 1/1996 | Lee et al. | |
| 5,492,442 A | 2/1996 | Lasner | |
| 5,501,695 A | 3/1996 | Anspach, Jr. et al. | |
| 5,501,696 A | 3/1996 | Trott | |
| 5,505,736 A | 4/1996 | Reimels et al. | |
| 5,520,692 A | 5/1996 | Ferrante | |
| 5,522,843 A | 6/1996 | Zang | |
| 5,522,844 A | 6/1996 | Johnson | |
| 5,534,011 A | 7/1996 | Greene, Jr. et al. | |
| 5,545,180 A | 8/1996 | Le et al. | |
| 5,549,617 A | 8/1996 | Green et al. | |
| 5,556,428 A | 9/1996 | Shah | |
| 5,562,664 A | 10/1996 | Durlacher et al. | |
| 5,562,672 A | 10/1996 | Huebner et al. | |
| 5,562,689 A | 10/1996 | Green et al. | |
| 5,569,305 A | 10/1996 | Bonutti | |
| 5,569,306 A | 10/1996 | Thal | |
| 5,571,139 A | 11/1996 | Jenkins, Jr. | |
| 5,573,547 A * | 11/1996 | LeVeen et al. | 606/232 |
| 5,573,548 A | 11/1996 | Nazre et al. | |
| 5,575,801 A | 11/1996 | Habermeyer et al. | |
| 5,575,819 A | 11/1996 | Amis | |
| 5,578,057 A | 11/1996 | Wenstrom, Jr. | |
| 5,584,835 A | 12/1996 | Greenfield | |
| 5,584,839 A | 12/1996 | Gieringer | |
| 5,591,207 A | 1/1997 | Coleman | |
| 5,593,410 A | 1/1997 | Vrespa | |
| 5,593,425 A | 1/1997 | Bonutti et al. | |
| 5,601,557 A | 2/1997 | Hayhurst | |
| 5,607,432 A | 3/1997 | Fucci | |
| 5,618,314 A | 4/1997 | Harwin et al. | |
| 5,624,446 A | 4/1997 | Harryman, II | |
| 5,626,613 A | 5/1997 | Schmieding | |
| 5,634,926 A | 6/1997 | Jobe | |

(56) References Cited

U.S. PATENT DOCUMENTS

| | | | |
|---|---|---|---|
| 5,637,112 A | 6/1997 | Moore et al. |
| 5,643,269 A | 7/1997 | Harle |
| 5,643,273 A | 7/1997 | Clark |
| 5,643,320 A | 7/1997 | Lower et al. |
| 5,643,321 A | 7/1997 | McDevitt |
| 5,645,545 A | 7/1997 | Bryant |
| 5,645,547 A | 7/1997 | Coleman |
| 5,645,589 A | 7/1997 | Li |
| 5,647,874 A | 7/1997 | Hayhurst |
| 5,658,313 A | 8/1997 | Thal |
| 5,662,658 A | 9/1997 | Wenstrom, Jr. |
| 5,665,112 A | 9/1997 | Thal |
| 5,667,509 A | 9/1997 | Westin |
| D385,352 S | 10/1997 | Bales et al. |
| 5,681,318 A | 10/1997 | Pennig et al. |
| 5,681,333 A | 10/1997 | Burkhart et al. |
| 5,683,401 A | 11/1997 | Schmieding et al. |
| 5,683,419 A | 11/1997 | Thal |
| 5,685,313 A | 11/1997 | Mayevsky |
| 5,690,649 A | 11/1997 | Li |
| 5,690,676 A | 11/1997 | DiPoto et al. |
| 5,690,677 A | 11/1997 | Schmieding et al. |
| 5,697,950 A | 12/1997 | Fucci et al. |
| 5,702,397 A | 12/1997 | Goble et al. |
| 5,702,398 A | 12/1997 | Tarabishy |
| 5,707,394 A | 1/1998 | Miller et al. |
| 5,709,708 A | 1/1998 | Thal |
| 5,720,765 A | 2/1998 | Thal |
| 5,720,766 A | 2/1998 | Zang et al. |
| 5,725,529 A | 3/1998 | Nicholson et al. |
| 5,725,541 A | 3/1998 | Anspach, III et al. |
| 5,728,136 A | 3/1998 | Thal |
| 5,733,307 A | 3/1998 | Dinsdale |
| 5,738,685 A | 4/1998 | Halm et al. |
| 5,741,300 A | 4/1998 | Li |
| 5,743,914 A | 4/1998 | Skiba |
| 5,749,878 A | 5/1998 | Bracy et al. |
| 5,755,721 A | 5/1998 | Hearn |
| 5,782,864 A | 7/1998 | Lizardi |
| 5,782,865 A | 7/1998 | Grotz |
| 5,792,142 A | 8/1998 | Galitzer |
| 5,797,963 A | 8/1998 | McDevitt |
| 5,810,854 A | 9/1998 | Beach |
| 5,814,051 A | 9/1998 | Wenstrom, Jr. |
| 5,814,071 A | 9/1998 | McDevitt et al. |
| 5,824,011 A | 10/1998 | Stone et al. |
| 5,827,291 A | 10/1998 | Fucci et al. |
| 5,843,087 A | 12/1998 | Jensen et al. |
| 5,843,127 A | 12/1998 | Li |
| 5,851,219 A | 12/1998 | Goble et al. |
| 5,860,978 A | 1/1999 | McDevitt et al. |
| 5,860,983 A | 1/1999 | Wenstrom, Jr. |
| 5,865,559 A | 2/1999 | Yang |
| 5,868,762 A | 2/1999 | Cragg et al. |
| 5,868,789 A | 2/1999 | Huebner |
| 5,879,372 A | 3/1999 | Bartlett |
| 5,885,294 A | 3/1999 | Pedlick et al. |
| 5,891,168 A | 4/1999 | Thal |
| 5,893,850 A | 4/1999 | Cachia |
| 5,902,321 A | 5/1999 | Caspari et al. |
| 5,911,721 A | 6/1999 | Nicholson et al. |
| 5,935,129 A | 8/1999 | McDevitt et al. |
| 5,948,000 A | 9/1999 | Larsen et al. |
| 5,948,001 A | 9/1999 | Larsen |
| 5,951,559 A | 9/1999 | Burkhart |
| 5,957,953 A | 9/1999 | DiPoto et al. |
| 5,964,764 A | 10/1999 | West, Jr. et al. |
| 5,964,783 A * | 10/1999 | Grafton et al. ............... 606/232 |
| 5,968,044 A | 10/1999 | Nicholson et al. |
| 5,980,558 A | 11/1999 | Wiley |
| 5,993,451 A | 11/1999 | Burkhart |
| 5,993,459 A | 11/1999 | Larsen et al. |
| 6,007,567 A | 12/1999 | Bonutti |
| 6,013,083 A | 1/2000 | Bennett |
| 6,022,373 A | 2/2000 | Li |
| 6,024,758 A | 2/2000 | Thal |
| 6,027,523 A | 2/2000 | Schmieding |
| 6,030,162 A | 2/2000 | Huebner |
| 6,036,694 A | 3/2000 | Goble et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,086,608 A | 7/2000 | Ek et al. |
| 6,096,041 A | 8/2000 | Gellman et al. |
| 6,117,162 A | 9/2000 | Schmieding et al. |
| 6,129,762 A | 10/2000 | Li |
| 6,143,017 A | 11/2000 | Thal |
| 6,149,669 A | 11/2000 | Li |
| 6,156,039 A | 12/2000 | Thal |
| 6,159,235 A | 12/2000 | Kim |
| 6,200,329 B1 | 3/2001 | Fung et al. |
| 6,214,031 B1 | 4/2001 | Schmieding |
| 6,221,107 B1 | 4/2001 | Steiner et al. |
| 6,231,592 B1 | 5/2001 | Bonutti et al. |
| 6,280,474 B1 | 8/2001 | Cassidy et al. |
| 6,287,324 B1 | 9/2001 | Yarnitsky et al. |
| 6,319,270 B1 | 11/2001 | Grafton et al. |
| 6,319,271 B1 | 11/2001 | Schwartz et al. |
| 6,355,053 B1 | 3/2002 | Li |
| 6,436,124 B1 | 8/2002 | Anderson et al. |
| RE37,963 E | 1/2003 | Thal |
| 6,508,830 B2 | 1/2003 | Steiner |
| 6,511,499 B2 | 1/2003 | Schmieding et al. |
| 6,517,542 B1 * | 2/2003 | Papay et al. ................... 606/232 |
| 6,520,980 B1 | 2/2003 | Foerster |
| 6,524,317 B1 | 2/2003 | Ritchart et al. |
| 6,527,772 B2 | 3/2003 | Enayati |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,558,389 B2 | 5/2003 | Clark et al. |
| 6,562,044 B1 | 5/2003 | Cooper |
| 6,585,730 B1 | 7/2003 | Foerster |
| 6,610,080 B2 | 8/2003 | Morgan |
| 6,635,074 B2 | 10/2003 | Bartlett |
| 6,641,596 B1 * | 11/2003 | Lizardi ........................ 606/232 |
| 6,641,597 B2 * | 11/2003 | Burkhart et al. .............. 606/232 |
| 6,652,561 B1 | 11/2003 | Tran |
| 6,652,563 B2 * | 11/2003 | Dreyfuss ....................... 606/232 |
| 6,656,183 B2 * | 12/2003 | Colleran et al. .............. 606/232 |
| 6,660,008 B1 | 12/2003 | Foerster et al. |
| 6,666,877 B2 * | 12/2003 | Morgan et al. ............... 606/232 |
| 6,692,516 B2 | 2/2004 | West, Jr. et al. |
| 6,699,250 B1 | 3/2004 | Österle et al. |
| 6,716,234 B2 | 4/2004 | Grafton et al. |
| 6,773,450 B2 * | 8/2004 | Leung et al. .................. 606/232 |
| 6,818,010 B2 | 11/2004 | Eichhorn et al. |
| 6,840,953 B2 | 1/2005 | Martinek |
| 6,857,520 B2 | 2/2005 | Salazar et al. |
| 6,916,333 B2 | 7/2005 | Schmieding et al. |
| 6,923,824 B2 | 8/2005 | Morgan et al. |
| 6,932,834 B2 | 8/2005 | Lizardi et al. |
| 7,037,324 B2 | 5/2006 | Martinek |
| 7,083,638 B2 | 8/2006 | Foerster |
| 7,204,839 B2 | 4/2007 | Dreyfuss et al. |
| 7,211,088 B2 | 5/2007 | Grafton et |
| 7,217,279 B2 | 5/2007 | Reese |
| 7,322,978 B2 * | 1/2008 | West, Jr. ........................ 606/60 |
| 7,329,272 B2 | 2/2008 | Burkhart et al. |
| 7,491,217 B1 | 2/2009 | Hendren et al. |
| 7,517,357 B2 | 4/2009 | Abrams et al. |
| 7,637,949 B2 | 12/2009 | Hart |
| 7,651,495 B2 | 1/2010 | McDevitt et al. |
| 7,695,495 B2 | 4/2010 | Dreyfuss |
| 7,785,347 B2 | 8/2010 | Harvie et al. |
| 7,803,173 B2 | 9/2010 | Burkhart et al. |
| 7,883,528 B2 * | 2/2011 | Grafton et al. ............... 606/232 |
| 7,883,529 B2 | 2/2011 | Sinnott et al. |
| 7,887,551 B2 | 2/2011 | Bojarski et al. |
| 7,981,140 B2 | 7/2011 | Burkhart |
| 7,993,369 B2 | 8/2011 | Dreyfuss |
| 8,343,186 B2 | 1/2013 | Dreyfuss et al. |
| 2001/0002439 A1 | 5/2001 | Bonutti et al. |
| 2001/0014814 A1 | 8/2001 | Bonutti et al. |

(56) References Cited

U.S. PATENT DOCUMENTS

| | | |
|---|---|---|
| 2001/0018613 A1 | 8/2001 | Huene |
| 2001/0021862 A1 | 9/2001 | Bonutti et al. |
| 2002/0013608 A1 | 1/2002 | ElAttrache et al. |
| 2002/0052629 A1* | 5/2002 | Morgan et al. ............... 606/232 |
| 2002/0087190 A1 | 7/2002 | Benavitz et al. |
| 2002/0111653 A1 | 8/2002 | Foerster |
| 2002/0128684 A1 | 9/2002 | Foerster |
| 2002/0147463 A1* | 10/2002 | Martinek ...................... 606/232 |
| 2002/0188305 A1 | 12/2002 | Foerster et al. |
| 2003/0004545 A1 | 1/2003 | Burkhart et al. |
| 2003/0065361 A1* | 4/2003 | Dreyfuss ...................... 606/232 |
| 2003/0069604 A1 | 4/2003 | Schmieding et al. |
| 2003/0144696 A1 | 7/2003 | Sinnott et al. |
| 2003/0149448 A1 | 8/2003 | Foerster et al. |
| 2003/0191498 A1 | 10/2003 | Foerster et al. |
| 2003/0195563 A1 | 10/2003 | Foerster |
| 2003/0204193 A1 | 10/2003 | Gabriel et al. |
| 2004/0030354 A1* | 2/2004 | Leung et al. .................. 606/232 |
| 2004/0093031 A1 | 5/2004 | Burkhart et al. |
| 2004/0106950 A1* | 6/2004 | Grafton et al. ................ 606/232 |
| 2004/0133239 A1 | 7/2004 | Singhatat |
| 2004/0138683 A1 | 7/2004 | Shelton et al. |
| 2004/0138706 A1 | 7/2004 | Abrams et al. |
| 2004/0267316 A1* | 12/2004 | Powell et al. ................. 606/231 |
| 2005/0222618 A1 | 10/2005 | Dreyfuss et al. |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2005/0283158 A1 | 12/2005 | West, Jr. |
| 2006/0004364 A1 | 1/2006 | Green et al. |
| 2006/0074434 A1 | 4/2006 | Wenstrom, Jr. et al. |
| 2006/0079904 A1 | 4/2006 | Thal |
| 2006/0100630 A1 | 5/2006 | West, Jr. |
| 2007/0142838 A1 | 6/2007 | Jordan |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0191849 A1 | 8/2007 | ElAttrache et al. |
| 2007/0225719 A1 | 9/2007 | Stone et al. |
| 2007/0255317 A1 | 11/2007 | Fanton et al. |
| 2007/0260259 A1 | 11/2007 | Fanton et al. |
| 2008/0004659 A1 | 1/2008 | Burkhart et al. |
| 2009/0187216 A1 | 7/2009 | Schmieding et al. |
| 2011/0015674 A1 | 1/2011 | Howard et al. |

FOREIGN PATENT DOCUMENTS

| | | |
|---|---|---|
| EP | 1016377 | 7/2000 |
| EP | 1530951 A2 | 5/2005 |
| EP | 1 762 186 A3 | 3/2007 |
| EP | 1797826 B1 | 12/2009 |
| FR | 2588332 | 4/1987 |
| FR | 2622430 | 10/1987 |
| SU | 1034734 | 8/1983 |
| WO | 99/37217 | 7/1999 |
| WO | 0221998 A2 | 3/2002 |
| WO | 2009055075 | 4/2009 |

OTHER PUBLICATIONS

"Bone Screw Technical Information," Richards Manufacturing Company, Inc. Tech. Publ. 1980, pp. 1-14.

"Implants for Surgery-Metal Bone Screws With Hexagonal Drive Connection, Spherical Under-Surface of Head, Asymmetrical Thread-Dimensions," International Standard ISO 5834, 1991(E), pp. 1-10.

Linvatec Revo Cancellous Screw Advertisement, 1993.

R.M. Altieri Mitek Surgical Products announces fourth-quarter and year-end results, Business Wire (Feb. 24, 1995).

Rupp et al., "Fatigue Testing of Suture Anchors," The American Journal of Sports Medicine, Mar. 2002, vol. 30, No. 2, pp. 239-247.

Laws, "Suturing Techniques," Principles of Laparoscopic Surgery, 1995, pp. 35-45.

Bacilla M.D., Phillip, "Arthroscopic Bankart Repair in a High Demand Patient Population", Arthroscopy: The Journal of Arthroscopic and Related Surgery, vol. 13, No. 1, Feb. 1997, pp. 51-60.

All Soft Tissue Anchors Are Not Created Equal . . . , Orthopaedic Biosystems Ltd., Inc., 1996.

M3-X Extremity Fixation System Just Drill and Drive, Osteomed Corporation, 1994.

Mitek GII Anchor™ System, Instrument Guide/Ordering Information, Mitek® Surgical Products, Inc., 1994.

Mitek GII Anchor™ System, Instrument Guide/Ordering Information, 1994.

Bradley M.D., James P., Labral Repair With Statak, Linvatec, 1994.

Your open techniques work . . . Let Our Arthroscopic Tools Work for You, Innovasive® Devices, Inc., 1995.

Snyder, M.D., Stephen, The Mini-Revo Labral Repair System, Linvatec, 1994.

Higgins, MD et al., Laurence D., Arthroscopic Bankart Repair, Operative Technique and Surgical Pitfalls, Clinics in Sports Medicine, vol. 19, No. 1, Jan. 2000, pp. 49-62.

Cole, MD MBA et al., Brian J., Arthroscopic Shoulder Stabilization With Suture Anchors: Technique, Technology, and Pitfalls, Clinical Orthopaedics and Related Research, vol. 390, Sep. 2001, pp. 17-30.

Barber, M.D., F. Alan et al., Internal Fixation Strength of Suture Anchors—Update 1997, Arthroscopy: The Journal of Arthroscopic and Related Surgery, vol. 13, No. 3 Jun. 1997, pp. 355-362.

\* cited by examiner

SECTION B-B
FIG.7a

SECTION C-C
FIG.8

SECTION A-A
FIG. 12

SUTURE ANCHOR WITH INSERT-MOLDED RIGID MEMBER

This application is a continuation-in-part of U.S. application Ser. No. 11/097,172, filed on Apr. 4, 2005, now U.S. Pat. No. 8,343,186. This application is also a continuation-in-part of U.S. application Ser. No. 10/083,568, filed on Feb. 27, 2002, now U.S. Pat. No. 7,226,469, which claims priority to U.S. Provisional Application No. 60/271,414, filed on Feb. 27, 2001, and which is a continuation-in-part of U.S. application Ser. No. 09/495,816, filed on Feb. 2, 2000, now U.S. Pat. No. 6,517,564, which claims priority to U.S. Provisional Application No. 60/118,228, filed on Feb. 2, 1999 and U.S. Provisional Application No. 60/125,781, filed on Mar. 23, 1999. This application is also a continuation-in-part of U.S. application Ser. No. 11/224,060, filed on Sep. 13, 2005. This application also claims priority to U.S. Provisional Application No. 60/715,614, filed on Sep. 12, 2005. The disclosures of all of the above-cited applications are incorporated by reference in their entirety.

FIELD OF THE INVENTION

The present invention relates to an apparatus for anchoring surgical suture to bone, and more particularly, to an apparatus using a suture anchor having a transverse anchor pin or an insert-molded eyelet shield.

BACKGROUND OF THE INVENTION

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include a structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Pat. No. 5,964,783.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking.

Further, there is a need for a suture eyelet shield within a biodegradable suture anchor with a bearing surface that will resist suture cut-through of the bioabsorbable material.

SUMMARY OF THE INVENTION

The suture anchor of the present invention overcomes the disadvantages of the prior art discussed above by providing, in one embodiment, a fully threaded suture anchor with an eyelet shield that is molded into the distal part of the biodegradable suture anchor. The eyelet shield of the present invention provides the strength necessary to secure the suture and also prevents suture cut-through.

The eyelet formed at the distal end is formed of a piece of suture or other material transversely insert-molded into the anchor so as to provide an eyelet shield. The shield provides a bearing surface that will resist suture cut-through.

In accordance with another embodiment of the invention, a ribbed suture anchor is provided with an eyelet shield at the proximal end. The eyelet shield is formed of a loop of suture material which is inserted molded within the suture anchor during the manufacturing process.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 1:
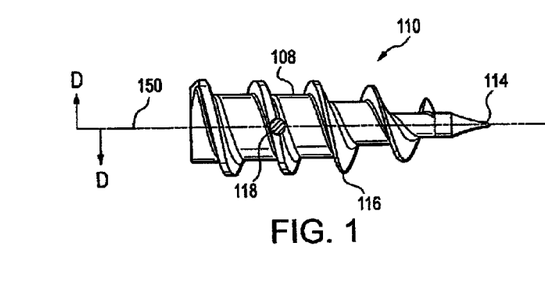
FIG. 1 is a side elevational view of the suture anchor according to an embodiment of the invention.

FIG. 1 illustrates a suture anchor according to a first preferred embodiment of the present invention, indicated generally by reference numeral 110. In the preferred embodiment, body 108 of anchor 110 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16°. The relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about five flights of thread, with the angle of the threads and other configurations of the anchor being similar to the suture anchor of U.S. Pat. No. 6,511,499, the disclosure of which is hereby incorporated by reference in its entirety.

Figure 3:
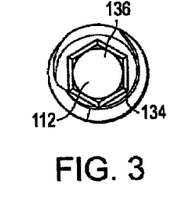
FIG. 3 is a proximal end view of the suture anchor of FIG. 1.

As can be seen more clearly with reference to FIG. 3, the proximal end portion of the anchor has a polygonally shaped bore 134, preferably hexagonal or square, having an opening 112 at the proximal end 92 of anchor body 108 and extending into the anchor body approximately one-third of the length thereof. Prior art anchors have sharp edges around the drive opening, which is problematic in that sutures passing through the central opening at the proximal end 92 of the anchor can be abraded by the sharp edges, thereby compromising the strength of the sutures. In the suture anchor of the present invention, the peripheral edges defining polygonally shaped opening 112 is smooth and rounded outwardly with no sharp edges. Preferably, the opening 112 forms a slight lip curving around the diameter of the bore 134. Thus, sutures threaded through the anchor 110, as will be discussed below, will not become frayed upon being pressed or rubbed against the anchor at the proximal opening 112.

Figure 2:
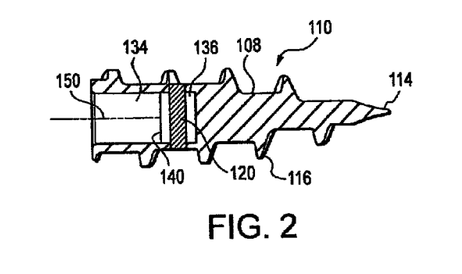
FIG. 2 is a longitudinal sectional view of the suture anchor shown in FIG. 1 through the plane D-D indicated therein.

As shown in FIG. 2, a cylindrical bore 136 having a diameter corresponding to that of the polygonally shaped bore 134 extends from the distal end of the polygonally shaped bore 134 to a position roughly halfway along the length of anchor body 108. The transition between polygonally shaped bore 134 and cylindrical bore 136 forms an annular shoulder 140, against which the distal end of a polygonal driver 202, preferably hexagonal or square, abuts when inserted into the polygonally shaped bore 134 to drive the anchor into bone.

Two longitudinal, diametrically opposite apertures 118 are formed in anchor body 108, the apertures 118 supporting a metal transverse anchor pin 120 which extends across cylindrical bore 136.

Figure 4A:
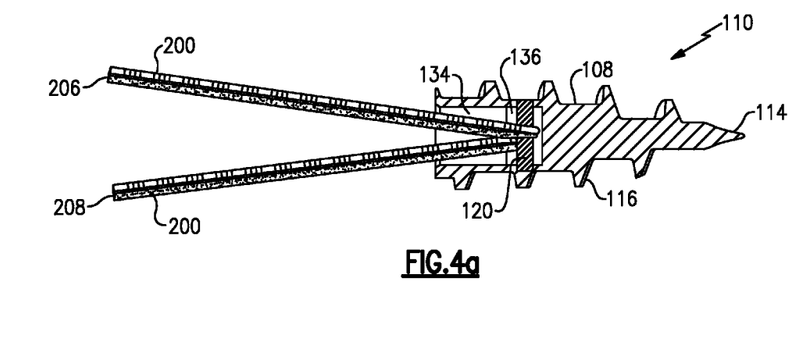
FIG. 4A is a cross sectional view of the suture anchor of FIG. 1 showing a suture looped over the transverse anchor pin.

As illustrated in FIGS. 1, 2 and 4a, apertures 118 extend through and interrupt the threads 116 around anchor body 108 at approximately one-third of the length of the anchor body from the proximal end 92 thereof. One or more sutures 200 are secured to the anchor by looping the suture(s) around metal anchor pin 120 as shown in FIG. 4a. Although the metal anchor pin 120 is illustrated in FIGS. 2 and 4a as oriented transversal to longitudinal axis 150 of the anchor body 108, the metal anchor pin 120 may form any angle with the longitudinal axis 150 and, thus, the invention is not limited to metal anchor pin 120 forming an angle of about ninety degrees with the longitudinal axis 150 of the anchor body 108.

Preferably, suture anchor 110 is formed of a hard biocompatible metal, such as a titanium alloy, but can be made of biocompatible materials other than metal. The suture secured to the anchor may be FiberWire suture, sold by Arthrex, Inc. of Naples, Fla.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is cast in a die, with the bores, passageways and apertures described above either being formed during the casting process or formed afterwards. If necessary, the distal tip 114 of the anchor 110 is trimmed to the desired length and the surfaces of the anchor are polished to the desired finish.

As mentioned above, the suture anchor 110 of the present invention may be installed in the bone without the need to pre-drill a hole in the bone. The suture anchor 110 is installed using a driver 202 having a shaft having a polygonal cross-section for at least a length equal to the length of the polygonal bore 134 from proximal opening 112 to the shoulder 140 inside the anchor 110. The driver 202 has a cannula 204 extending through the entire length thereof, with openings 216 and 214 at the proximal end and the distal end, respectively, thereof. Of course, the outer diameter of the polygonal shaft is sized to fit inside the polygonal bore in the anchor so as to be enabled to drive the same.

Figure 4B:
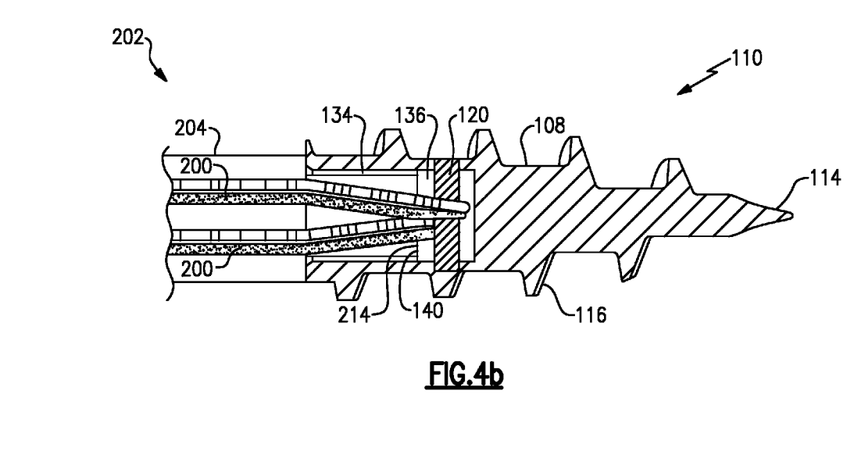
FIG. 4B is a cross sectional view of the suture anchor of FIG. 1 showing a portion of a polygonal driver inserted into a polygonally shaped bore of the suture anchor.
Figure 4C:
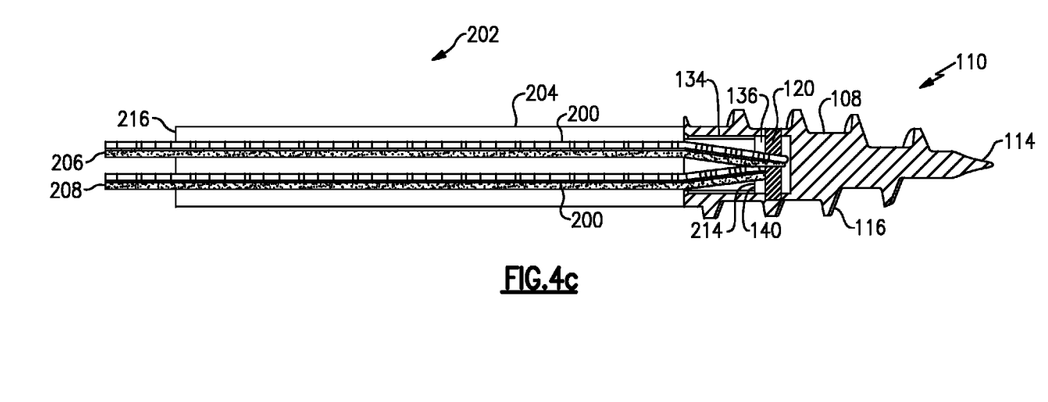
FIG. 4C is a cross sectional view of the suture anchor of FIG. 1 showing the polygonal driver inserted into a polygonally shaped bore of the suture anchor.

As shown in FIGS. 4b and 4c, with the desired number of suture strands 200 threaded around the anchor pin 120 in the suture anchor 110, the ends 206 and 208 of the suture strands 200 are threaded through the cannula 204 in the polygonal driver 202 from the distal end thereof and extend from the proximal opening 216 thereof. The distal end of the polygonal driver 202 is inserted into the proximal end 92 of the anchor 110. With the distal end of the driver 202 abutting the shoulder 140 and the anchor 110 positioned at the location at which it is to be installed, the polygonal driver 202 is rotated to drive the anchor 110 into the bone until the proximal surface of the anchor 110 is flush with the surface of the bone.

Since it is not necessary for the proximal end 92 of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Figure 5:
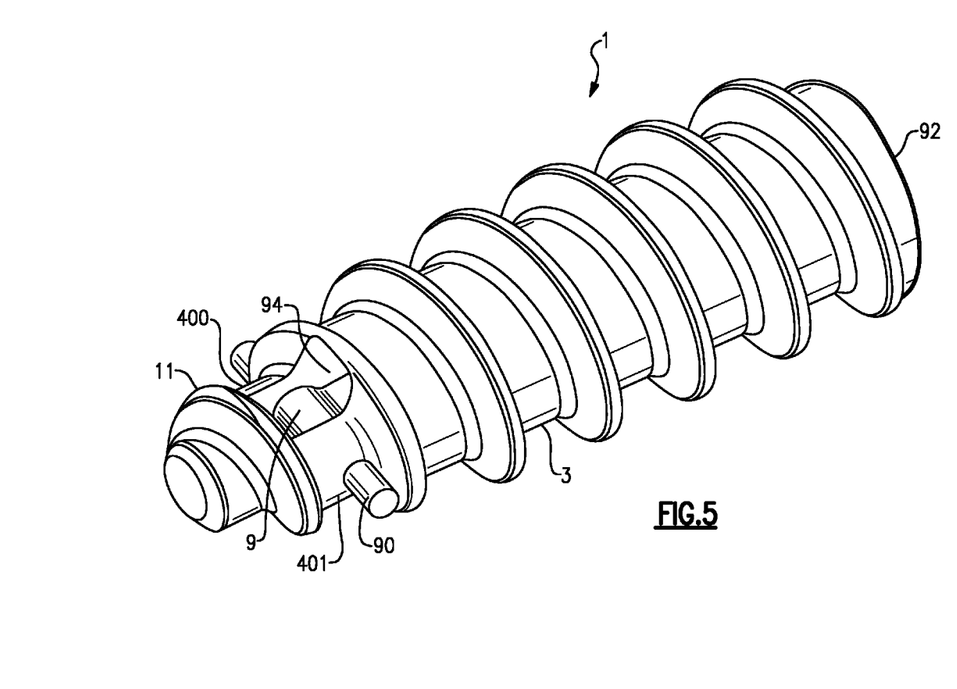
FIG. 5 is a perspective representation of the suture anchor according to another embodiment of the invention.

Referring to FIG. 5, a suture anchor 1 is shown in perspective in accordance with another embodiment of the invention. In this embodiment, the suture anchor 1 has a fully-threaded body 3. The suture anchor 1 may be comprised of any material. Preferably, the suture anchor 1 is formed of a bioabsorbable material. Rather than having an anchor pin as discussed in the embodiment above, the suture anchor 1 has an eyelet shield 9 molded transversely into a distal part 11 of the threaded body 3 of the suture anchor 1. Eyelet shield 9 is shown as a bar, however, any appropriate type of material may be used, including bioabsorbable material or a length of suture, for example. The eyelet shield 9 can include of a length of suture 90 molded transversely into distal part 11 of threaded body 3. Although the shield 9 is illustrated as being transverse to the longitudinal axis of suture anchor 1, the shield 9 may also be formed at any angle with respect to the longitudinal axis and, thus, the invention is not limited to shield 9 formed at angle of about ninety degrees with the longitudinal axis of the suture anchor 1.

Figure 6:
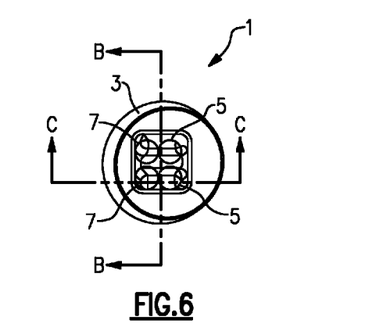
FIG. 6 is an end view of the suture anchor shown in FIG. 5.
Figure 7A:
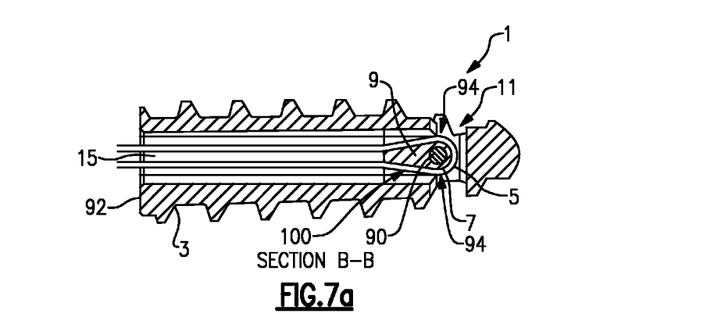
FIG. 7A is an elevational cross-section of the suture anchor of FIG. 6 through the plane B-B indicated therein.
Figure 7B:
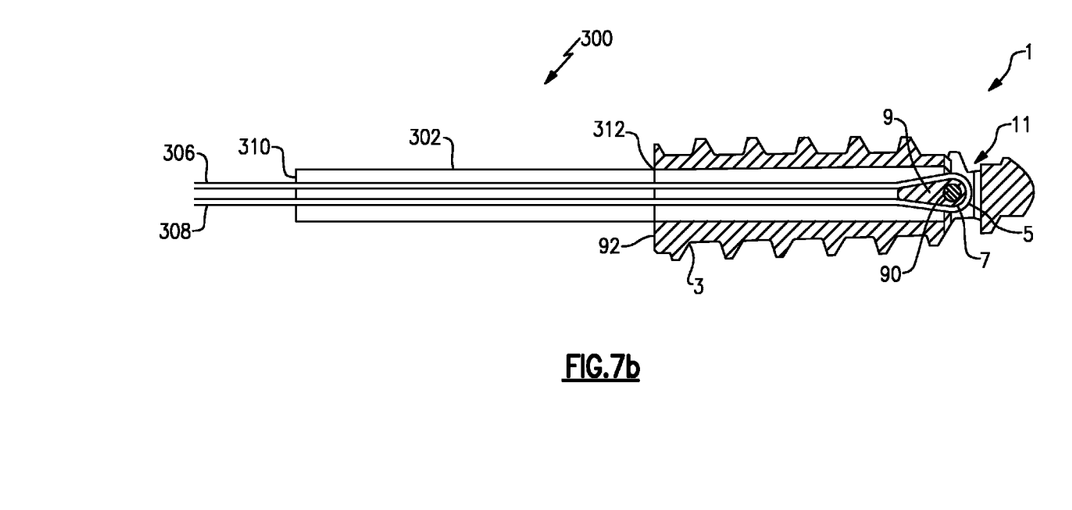
FIG. 7B is an elevational cross-section of the suture anchor of FIG. 6 through the plane B-B indicated therein showing a portion of a driver inserted into a bore of a suture anchor.
Figure 8:
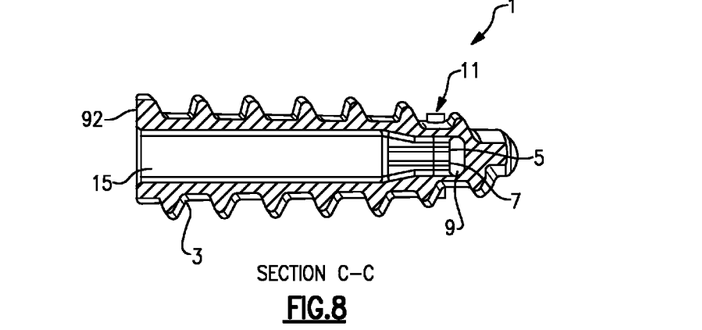
FIG. 8 is a cross-section in plan view of the suture anchor of FIG. 6 through the plane C-C indicated therein.

As illustrated in FIGS. 6-8, two strands of tie-down sutures 5, 7 are threaded around the eyelet shield 9 of the distal end 11 of the suture anchor 1 and threaded into a suture passage 94. In one example, there is a suture passage 94 on opposing sides of the shield 9. The shield 9 provides a bearing surface around which sutures 5, 7 are threaded and disposed. The sutures 5, 7 are threaded through a bore 15 and disposed about the shield 9 and have ends 306 and 308 that extend out of the proximal end 92 of the anchor 1. The bore 15 extends from the proximal end 92 of the suture anchor 1 to a location roughly halfway along the anchor body 1. As discussed above, the bore 15 has an opening at the proximal end 92 of the suture anchor and is shaped to accommodate a driver head for driving the suture anchor.

The eyelet shield 9 resists suture cut-. Further, the shield 9 provides the strength necessary to secure the sutures 5, 7. In addition, because the eyelet shield is molded transversely into the distal end of the suture anchor, this provides greater security to prevent pull-out of the suture from within the suture anchor or from an anchor pin, which could loosen. The eyelet shield also prevents the suture from fraying.

Although a fully-threaded suture anchor 1 with threaded body 3 is shown, the anchor does not necessarily have to be fully threaded. As discussed above, the suture anchor also need not be a threaded device, but can also be formed as a tap-in type anchor. In addition, sutures 5, 7 can be insert-molded into the anchor to prevent saw-through.

The suture anchor 1 is installed using a driver 300. The driver 300 has a cannula 302 with openings at the proximal and distal ends thereof. As shown in FIGS. 7A and 7B, with the desired number of sutures 5 and 7 threaded around the shield 9 in the suture anchor 1, ends 306 and 308 of the sutures 5 and 7 are threaded through the cannula 302 in the driver 300 from a distal end 310 thereof and extend from the proximal opening 312 thereof. The distal end of the driver 300 is inserted into the proximal end 92 of the anchor 1, and the driver 300 is rotated to drive the anchor 1 into the bone until the proximal surface of the anchor 1 is flush with the surface of the bone.

In another embodiment, as illustrated in FIGS. 9-12, a push-in suture anchor 20 is shown having suture 22 that is insert-molded longitudinally into the suture anchor body 24 during the manufacturing process.

Figure 9:
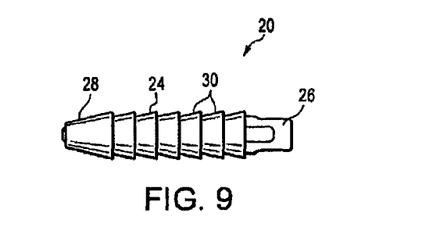
FIG. 9 is a plan view of the push-in suture anchor according to another embodiment of the invention.
Figure 10:
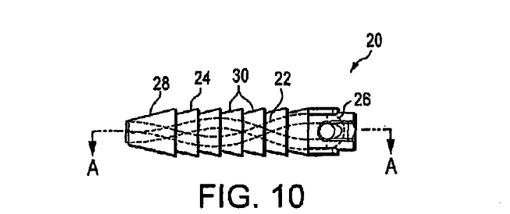
FIG. 10 is a plan view of the push-in suture anchor of FIG. 9 showing a suture insert-molded within the suture anchor.
Figure 11:
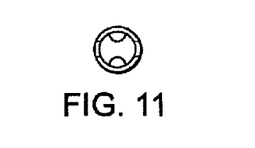
FIG. 11 is a proximal end view of the suture anchor of FIG. 9.
Figure 12:
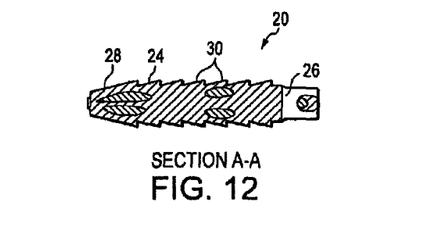
FIG. 12 is a longitudinal sectional view of the suture anchor shown in FIG. 9 through the plane A-A, indicated therein.

The suture anchor body 24 preferably is formed of a bioabsorbable material, poly(l-lactide-co-d, l-lactide) 70:30 (PLDLA) being most preferred. Suture 22 can be any known type of suture selected according to the size of the anchor and the anticipated application. The suture 22 preferably is No. 2 polyester braided suture.

At least one length of the insert-molded suture 22 extends from the proximal end 92 of the suture anchor body 24. Preferably, the suture 22 extends from the suture anchor body 24 in the form of a loop. The suture 22 is insert-molded into the suture anchor body 24 and also into the loop or eyelet 26. Various devices provide a suture anchor with a loop formed of a suture material, as disclosed in U.S. Publication No. 2002/0087190 and U.S. application Ser. No. 11/224,060, the entire disclosures of which are incorporated by reference herein. However, the suture loops disclosed in these applications are not encapsulated—this results in friction between the suture loop and a suture threaded through the loop. In the present invention, the suture 22, being insert-molded within the loop 26, eliminates suture against suture friction and provides better support and strength for a suture threaded through the loop.

The distal end 28 of the suture anchor body 24 tapers to a blunt tip. Suture anchor 20 is provided with slotted ribs 30 formed circumferentially at least partially around and partially along the length of body 24. Ribs 30 have a truncated, conical anchor at an angle of preferably 15° with respect to the longitudinal axis of anchor 20, and reaching a major diameter of 3.0 mm.

Although PLDLA is the most preferred material for the suture anchor of the present invention, other bioabsorbable materials known in the art can be utilized. As used herein, bioabsorbable is considered to be interchangeable with biodegradable, resorbable, and absorbable to mean that the device can be at least partially absorbed by the body over time. Preferably, the anchor material is selected so as to absorb or degrade substantially completely within 12-16 months of implantation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A suture anchor comprising:
   an anchor body having a longitudinal axis, a proximal end, a distal end, a central passage, a first suture opening, and a second suture opening, wherein the central passage extends along the longitudinal axis, the central passage extends from the first suture opening which is located at the proximal end of the anchor body and through a portion of a length of the anchor body, the first suture opening is encircled by a perimeter of the anchor body, and the second suture opening extends through a portion of the anchor body;

a rigid support fixed to the anchor body, wherein the rigid support extends across the central passage and has a first portion and a second portion spaced from the first portion, the first portion branching from a first wall portion of the anchor body and the second portion branching from a second wall portion of the anchor body, the rigid support spaced axially away from the first suture opening along the longitudinal axis of the anchor body, and the second suture opening is disposed near the rigid support; and at least one suture strand threaded into the central passage, wherein the at least one suture strand is supported by the rigid support and threaded through the first suture opening and the second suture opening of the anchor body.

2. The suture anchor according to claim 1, wherein the second suture opening is defined in part by the rigid support and a portion of the anchor body.

3. The suture anchor according to claim 2, including a third suture opening extending through the anchor body, wherein the third suture opening is disposed distal of the second suture opening, and the at least one suture strand is disposed in the first suture opening, the second suture opening, and the third suture opening.

4. The suture anchor according to claim 3, wherein the third suture opening forms in part a suture passage that extends across the longitudinal axis of the anchor body.

5. The suture anchor according to claim 3, wherein the at least one suture strand follows a path beginning with a first end of the at least one suture strand outside of the anchor body, through the first suture opening, through the central passage, through the second suture opening, through the third suture opening, around the rigid support, back through the central passage, back through the first suture opening, and ending at a second end of the at least one suture strand outside of the anchor body.

6. The suture anchor according to claim 1, wherein the at least one suture strand follows a path beginning with a first end of the at least one suture strand outside of the anchor body, through the first suture opening, through the central passage, through the second suture opening, around the rigid support, back through the central passage, back through the first suture opening, and ending at a second end of the at least one suture strand outside of the anchor body.

7. The suture anchor according to claim 1, wherein the second suture opening is located in a distal half of the anchor body, and the distal half includes the distal end of the anchor body.

8. The suture anchor according to claim 1, wherein the suture anchor and the rigid support are made of the same material.

9. The suture anchor according to claim 1, wherein the second suture opening forms in part a suture passage that extends along the longitudinal axis of the anchor body to the first suture opening.

10. A suture anchor assembly comprising:

an anchor body including a longitudinal axis, a proximal end, a distal end, and a central passage extending along the longitudinal axis from an opening at the proximal end of the anchor body through a portion of a length of the anchor body, wherein the opening is a first suture opening, the anchor body including a second suture opening disposed distal of the first suture opening, and a third suture opening disposed distal of the second suture opening, wherein a helical thread defines a perimeter at least around the proximal end of the anchor body;

a rigid support extending across the central passage, the rigid support having a first portion and a second portion spaced from the first portion, the first portion branching from a first wall portion of the anchor body and the second portion branching from a second wall portion of the anchor body, wherein the third suture opening is disposed distal of the rigid support;

at least one suture strand having a suture length threaded into the central passage, supported by the rigid support, and threaded past the proximal end of the anchor body, wherein at least a portion of the at least one suture strand is disposed in the central passage between the rigid support and the opening at the proximal end, and the at least one suture strand is disposed in the first suture opening, the second suture opening, and the third suture opening; and a driver including a shaft having a shaft length, wherein the shaft engages the anchor body, and the suture length of the at least one suture strand is greater than the shaft length of the shaft.

11. A suture anchor assembly comprising:

an anchor body including a distal end, a proximal end having, an opening, a central longitudinal axis, a first wall portion, a second wall portion spaced opposite to the first wall portion, and a suture passage beginning at the proximal end of the anchor body, wherein the suture passage extends about the central longitudinal axis, and the suture passage extends from the opening located at the proximal end of the anchor body and at least partially along a length of the anchor body, wherein the opening is a first suture opening that is encircled by a perimeter of the anchor body, a second suture opening extends through a portion of the anchor body, and a third suture opening extends through the anchor body, wherein the third suture opening is disposed distal of the second suture opening;

a rigid support integral with the anchor body to define a single-piece component, wherein the rigid support extends across the suture passage and has a first portion and a second portion spaced from the first portion, the first portion branching from the first wall portion of the anchor body and the second portion branching from the second wall portion of the anchor body, and the rigid support is spaced axially away from the opening at the proximal end along the central longitudinal axis; and at least one suture strand threaded into the suture passage, supported by the rigid support, and having ends that extend past the proximal end of the anchor body, and the at least one suture strand is disposed in the first suture opening, the second suture opening, and the third suture opening.

* * * * *

UNITED STATES PATENT AND TRADEMARK OFFICE
CERTIFICATE OF CORRECTION

| | |
|---|---|
| PATENT NO. | : 8,821,541 B2 |
| APPLICATION NO. | : 11/518872 |
| DATED | : September 2, 2014 |
| INVENTOR(S) | : Peter J. Dreyfuss et al. |

It is certified that error appears in the above-identified patent and that said Letters Patent is hereby corrected as shown below:

IN THE CLAIMS:

In claim 2, column 7, line 20; delete "a" and replace with --the--

In claim 10, column 8, line 16; delete "haying" and replace with --having--

In claim 11, column 8, line 31; after "having" delete ","

Signed and Sealed this
Ninth Day of December, 2014

Michelle K. Lee
*Deputy Director of the United States Patent and Trademark Office*